United States Patent [19]
Aono et al.

[11] Patent Number: 5,185,309
[45] Date of Patent: Feb. 9, 1993

[54] FLUID CATALYST FOR USE IN GAS PHASE OXIDATION OF AROMATIC HYDROCARBONS

[75] Inventors: Toshinao Aono, Chiba; Yukio Asami; Noboru Hirooka, both of Tokyo; Yusaku Arima, Onga; Susumu Fujii, Kitakyushu, all of Japan

[73] Assignee: Kawasaki Steel Corp., Hyogo, Japan

[21] Appl. No.: 673,962

[22] Filed: Mar. 22, 1991

[30] Foreign Application Priority Data

Mar. 27, 1990 [JP] Japan ..................... 2-77233

[51] Int. Cl.$^5$ ................ B01J 21/02; B01J 21/06; C07D 307/89
[52] U.S. Cl. ..................... 502/202; 549/248; 549/249; 502/350
[58] Field of Search .......................... 502/202

[56] References Cited

U.S. PATENT DOCUMENTS

| | | | |
|---|---|---|---|
| 3,806,469 | 4/1974 | Morita et al. | 502/202 |
| 3,843,552 | 10/1974 | Jouy et al. | 502/202 |
| 4,397,768 | 8/1983 | Felice | 502/202 |

FOREIGN PATENT DOCUMENTS

| | | | |
|---|---|---|---|
| 7225871 | 3/1973 | France. | |
| 110986 | 9/1978 | Japan | 502/202 |
| 1129475 | 10/1968 | United Kingdom | 502/202 |
| 2106414A | 4/1983 | United Kingdom. | |

OTHER PUBLICATIONS

European Search Report (3 pages).

*Primary Examiner*—Paul E. Konopka
*Attorney, Agent, or Firm*—Bierman and Muserlian

[57] ABSTRACT

A high activity and high selectivity fluid catalyst for use in gas phase oxidation of aromatic hydrocarbons, comprising 50 to 95% by weight (calculated by TiO$_2$+SiO$_2$+B$_2$O$_3$) of component (A) which comprises titanium oxide, silicon dioxide and boron oxide and 5 to 50% by weight [calculated by V$_2$O$_5$+M$_2$O (M represents an alkali metal)+SO$_3$] of component (B) comprising vanadium oxide, an alkali metal oxide and sulfuric anhydride, wherein weight ratios of B$_2$O$_3$ to TiO$_2$ and SiO$_2$ to TiO$_2$ in said component (A) are in the range of from 0.02 to 0.5 and from 0.25 to 1.0, respectively, is provided.

8 Claims, No Drawings

FLUID CATALYST FOR USE IN GAS PHASE OXIDATION OF AROMATIC HYDROCARBONS

FIELD OF THE INVENTION

This invention relates to fluid catalysts for use in the production of carboxylic anhydrides from aromatic hydrocarbons. More particularly, it relates to a fluid catalyst for use in the production of phthalic anhydride from a hydrocarbon material such, especially, as o-xylene or naphthalene by means of gas phase oxidation. It also relates to a process for the production of the fluid catalyst.

BACKGROUND OF THE INVENTION

Carboxylic anhydrides are produced by gas phase oxidation of aromatic hydrocarbon materials, with a typical example being the production of phthalic anhydride from o-xylene or naphthalene.

For use in the production of phthalic anhydride from o-xylene by means of fixed bed gas phase oxidation, various catalysts have been reported (for example, Practical catalysts for Respective Reactions, p. 358, 1970, edited by Kimio Tarama, published by Kagaku Kogyo-sha, Japan) including a combination of vanadium pentoxide with titanium oxide (anatase type), a combination of vanadium pentoxide with other active metal oxide such as tellurium oxide, molybdenum oxide, tungsten oxide, nickel oxide, niobium oxide, tin oxide, chromium oxide or the like, and a combination of vanadium pentoxide with an alkai metal salt such as of potassium, lithium, sodium or the like, supported on inert carriers such as Alundum, silicon carbide, quartz, pumice, α-alumina and the like.

In the case of a gas phase oxidation process in which a fixed catalyst bed is employed, excessively high heat generated by exothermic oxidation reaction is removed by employing a system in which a catalyst is uniformly packed into several thousands of reactor pipes, each having a small diameter of about 1 inch, and the exterior of the pipes is filled with a heat transfer medium for cooling use. This system, however, requires considerable labor and cost to complete uniform packing of a catalyst into each of such a massive number of reactor pipes, as well as great burdens of the cost of equipment and the operation management to maintain pressure loss and temperature of each of these reactor pipes at constant levels. This system also requires considerable labor and cost when deteriorated catalyst is replaced by fresh catalyst.

Also, a catalyst in which active components are coated on an inert carrier is apt to cause a run-away reaction triggered by ununiformity of reaction due to channeling of reaction gas, formation of hot spots, increased pressure loss and the like caused by peeling and release of the active components from the carrier during packing of the catalyst or at the time of the operation. In addition, high productivity cannot be attained by the use of the fixed bed process because concentration of a reaction gas must be maintained within its explosion limit and, therefore, the reaction gas can be supplied only at a low concentration level.

For the purpose of solving such problems, it is preferable to perform gas phase oxidation using a fluidized catalyst bed.

Compared to the aforementioned fixed bed process, such a fluidized bed process is markedly advantageous, because not only generated heat by the exothermic oxidation reaction can be removed easily but also channeling of the flow of material gas and formation of hot spots both of which are common in the case of the fixed bed process can be avoided. Another advantage of the fluidized bed process is that exchange and supplement of a catalyst can be made with less labor and cost. The fluid bed process still has a great advantage from a view point of productivity because of a possibility to increase concentration of a reaction material.

For use in the production of phthalic anhydride from o-xylene by means of gas phase oxidation, as well as the case of using naphthalene as the starting material, various fluid catalysts have been reported, for example in B.P. 941,293 (1963) and U.S. Pat. No. 3,232,955 (1966), such as a combination of vanadium pentoxide with potassium sulfate and other combinations with molybdenum oxide, tungsten oxide, phosphorus oxide, boron oxide and the like supported on silica. The use of such silica-supported catalyst, however, causes excess oxidation reaction and side reactions which results in the formation of CO and $CO_2$, thus making it difficult to obtain phthalic anhydride in a high yield. In order to improve the phthalic anhydride yield, attempts to mix the reaction gas with a halogen gas such as $Br_2$ have been reported for example in D.P. 1,144,709 (1963) and U.S. Pat. No. 3,455,962 (1969), but the use of such a halogen gas causes corrosion of equipment and therefore results in operational troubles.

A number of catalysts in which titanium oxide is used as a carrier and vanadium pentoxide is supported on the carrier have been proposed for example in B.P. 1,067,726 (1967) and Fr.P. 1,537,351 (1968). A catalyst having certain mechanical strength can be obtained by making a fused body of titanium oxide and vanadium pentoxide together with ammonium thiocyanate or an alkali compound. However, specific surface area and pore volume of the catalyst decrease by the formation of fused body, thus resulting in significant reduction of the catalytic activity. Because of the reduced activity, such a fused catalyst requires a high reaction temperature which causes excess oxidation and side reactions. In consequence, it is difficult to obtain phthalic anhydride with a high yield by the use of the fused catalyst.

In addition, since the formation of a fused body results in a catalyst having markedly high bulk density amplified by the high specific gravity of titanium oxide, it is difficult to perform efficient fluidized bed reaction using such a high bulk density catalyst.

Because of these reasons, production of phthalic anhydride from o-xylene by means of a fluidized bed gas phase oxidation reaction has not been put into practical use.

SUMMARY OF THE INVENTION

In view of the above, it therefore becomes an object of the present invention to provide a catalyst for use in a fluidized bed process for the production of phthalic anhydride from o-xylene or naphthalene by means of a gas phase oxidation reaction, a process which is greatly advantageous compared to a fixed bed process, as well as to provide a process for the production of such a fluid catalyst. More specific object of the present invention contemplates the provision of a high activity and high selectivity catalyst for use in a fluidized bed process, in which a mixture of titanium oxide silicon dioxide and boron oxide is used as a support or carrier and which has sufficient strength and appropriate bulk density.

The inventors of the present invention have conducted intensive studies on the development of a fluid catalyst containing titanium oxide as the main component, which is useful for the production of phthalic anhydride. This invention has been accomplished as a result of these efforts.

According to a first aspect of the present invention, there is provided a fluid catalyst for use in gas phase oxidation of aromatic hydrocarbons comprising 50 to 95% by weight (calculated by $TiO_2 + SiO_2 + B_2O_3$) of component (A) which comprises titanium oxide, silicon dioxide and boron oxide and 5 to 50% by weight [calculated by $V_2O_5 + M_2O$ (M represents an alkali metal) $+SO_3$] of component (B) comprising vanadium oxide, an alkali metal oxide and sulfuric anhydride, wherein weight ratios of $B_2O_3$ to $TiO_2$ and $SiO_2$ to $TiO_2$ in the component (A) are in the range of from 0.02 to 0.5 and from 0.25 to 1.0, respectively.

According to a second aspect of the present invention, there is provided a process for the production of the just described fluid catalyst, which comprises the steps of (a) mixing compounds as respective sources of titanium oxide, silicon dioxide, boron oxide, vanadium oxide, alkali metal oxide, and sulfuric anhydride, simultaneously or in an optional combination, (b) spray drying the mixture of step (a) and (c) calcinating spray-dried powder of step (b). Preferably, the source of titanium oxide is a titanium hydroxide which is capable of forming titanium oxide having a crystallite diameter of not more than 30 nm when dried at a temperature of about 300° C.

According to a third aspect of the present invention, there is provided a process for the production of a carboxylic anhydride which comprises performing gas phase oxidation of an aromatic hydrocarbon in the presence of the fluid catalyst.

Other objects and advantages of the present invention will be made apparent as the description progresses.

DETAILED DESCRIPTION OF THE INVENTION

A fluid catalyst of the present invention for use in gas phase oxidation of aromatic hydrocarbons comprises:

50 to 95% by weight (calculated by $TiO_2 + SiO_2 + B_2O_3$) of component (A) which comprises titanium oxide, silicon dioxide and boron oxide and 5 to 50% by weight [calculated by $V_2O_5 + M_2O$ (M represents an alkali metal) $+SO_3$] of component (B) comprising vanadium oxide, an alkali metal oxide and sulfuric anhydride, wherein weight ratios of $B_2O_3$ to $TiO_2$ and $SiO_2$ to $TiO_2$ in the component (A) are in the range of from 0.02 to 0.5 and from 0.25 to 1.0, respectively.

Amounts of the component (A) as a carrier in the catalyst if smaller than 50% by weight may not be preferable, because a catalyst having an appropriate bulk density which is suitable for use in a fluidized bed process will not be obtained and the activity of the catalyst will decrease. If amounts of the component (A) are larger than 95% by weight, amounts of the component (B) which is the source of active components in the catalyst will conversely ba reduced and, therefore, a desired catalytic activity will not be obtained. Preferable amount of the component (A) in the catalyst may be in the range of from 60 to 90% by weight, more preferably from 75 to 90% by weight.

In the component (A), a weight ratio of $B_2O_3/TiO_2$ may be in the range of from 0.02 to 0.5, preferably from 0.05 to 0.3, and that of $SiO_2/TiO_2$ may be in the range of from 0.25 to 1.0, preferably from 0.3 to 0.9.

If the $B_2O_3/TiO_2$ weight ratio is smaller than 0.02, effects of the addition of boron oxide on the improvement of abrasion resistance and selectivity for reaction products of the catalyst will not be attained. The weight ratio if larger than 0.5 may not be preferable, because the catalytic activity will decrease markedly, though the effect on the improvement of abrasion resistance will not decrease.

If the $SiO_2/TiO_2$ weight ratio is smaller than 0.25, bulk density of the resulting catalyst will increase and, therefore, a catalyst suitable for us: in a fluidized bed process will not be obtained. The weight ratio if larger than 1.0 may not be preferable, because specific surface area of the resulting catalyst will become large and selectivity of the catalyst will decrease.

The component (B) as active component in the catalyst may be used in an amount of from 5 to 50% by weight, preferably from 10 to 40% by weight, more preferably from 10 to 30% by weight, calculated by a form of "$V_2O_5 + M_2O$ (M is an alkali metal) $+SO_3$".

Amounts of the component (B) in the catalyst if smaller than 5% by weight would show no sufficient catalytic activity, and if larger than 50% by weight would reduce not only the catalytic activity but also fluidity because of considerable reduction of specific surface area of the resulting catalyst, deterioration of dispersion conditions of the active component and deposition of crystals in the catalyst.

Vanadium compound as a member of the component (B) may preferably be contained in the catalyst in an amount of from 1 to 30% by weight, more preferably from 1 to 15% by weight, calculated by a form of $V_2O_5$.

In the component (B), a molar ratio of $SO_3$ to $M_2O$ ($SO_3/M_2O$) may be in the range of from 0.1 to 6.0, preferably from 1.0 to 4.0, and a molar ratio of $M_2O$ to $V_2O_5$ ($M_2O/V_2O_5$) may be in the range of from 0.1 to 5.0, preferably from 0.3 to 3.0.

According to the present invention, the fluid catalyst for gas phase oxidation use may further contain a third component such as a rare earth compound in addition to the components (A) and (B).

According to another aspect of the present invention, there is provided a process for the production of a fluid catalyst containing titanium oxide, silicon dioxide, vanadium oxide, an alkali metal oxide, sulfuric anhydride and boron oxide as main components, which comprises the steps of (a) mixing compounds as respective sources of titanium oxide, silicon dioxide, boron oxide, vanadium oxide, alkali metal oxide, and sulfuric anhydride, (b) spray drying the mixture of step (a) and (c) calcinating spray-dried powder of step (b). Preferably, the source of titanium oxide is a titanium hydroxide which is capable of forming titanium oxide having a crystallite diameter of not more than 30 nm when dried at a temperature of about 300° C.

The material for use in the production process of a catalyst of the present invention is a solution or a suspension of respective sources of titanium oxide, silicon dioxide, vanadium oxide, an alkali metal oxide, sulfuric anhydride and boron oxide.

Preferably, the source of titanium oxide eligible for use in the present invention is a titanium hydroxide which is capable of forming titanium oxide having a crystallite diameter of not more than 30 nm when dried at a temperature of about 300° C. The term "crystallite diameter" as used herein means a value calculated using the following formula, based on a half-width of a diffraction peak of $2\theta=25.3°$ (Cu K$\alpha$ line) for anatase type titanium oxide in an X-ray diffraction pattern measured in accordance with the Debye-Scherrer's method.

$$\text{Crystallite diameter (nm)} = \frac{8.15}{\sqrt{B^2 - 0.0225}}$$

$$\left(B = \frac{\text{half-width (mm)}}{10}\right)$$

A catalyst containing titanium oxide which has a crystallite diameter of larger than 30 nm may have markedly low abrasion resistance compared to that having a crystallite diameter of not more than 30 nm. The use of such a catalyst containing large crystallite diameter titanium oxide in a fluidized bed system, therefore, will result in the discharge or scattering of the catalyst to a high degree which not only is uneconomical but also causes blocking tubes of a cyclone and a heat exchanger. Also, the use of such a catalyst will cause mixing of a large amount of the catalyst into a reaction product and also will make it difficult to keep a reaction gas in a proper state of fluidity. In addition, when crystallite diameter of titanium oxide in a catalyst exceeds 30 nm, specific surface area of titanium oxide conversely becomes small which will render uniform and sufficient distribution of an active component on the surface unattainable and therefore will result in markedly decreased catalytic activity. In consequence, satisfactory yield of a carboxylic anhydride may not be obtained when such a catalyst is used, even in the case of a fluidized bed gas phase oxidation process with a prolonged contact time.

The term "a titanium hydroxide which is capable of forming titanium oxide having a crystallite diameter of not more than 30 nm when dried at a temperature of about 300° C." as used herein is intended to include not only wet (water containing) titanium compounds which are generally called titanium hydroxide, metatitanic acid, orthotitanic acid, titania sol, titania gel and the like but also powder preparations obtained by drying them at a low temperature.

A titanium oxide source (or titanium hydroxide) eligible for use in the present invention may be obtained from any material or by any preparation method, provided that a crystallite diameter of titanium oxide in powder when dried at about 300° C. is not more than 30 nm, preferably 20 nm or smaller, more preferably 10 nm or smaller.

Examples of the source of titanium oxide (or titanium hydroxide) include a titan-c acid which is obtained by thermal hydrolysis during an intermediate step of a process for the production of titanium oxide for pigment use, and a titania sol preparation which is obtained by adding an acid to the titanic acid. Also included are titanium hydroxides, titania sol preparations and the like which are obtained by means of a neutralization hydrolysis or an ion exchange deoxidation hydrolysis of titanium sulfate, titanyl sulfate, titanium tetrachloride and the like Especially, a titanium hydroxide obtained from a solution of titanyl sulfate or the like by means of a neutralization hydrolysis at a low temperature of 40° C. or below may be most useful as a material for the production of a catalyst of the present invention, because its crystallite diameter when dried at about 300° C. is only several nm.

Examples of titanium oxide sources which form titanium oxide having a crystallite diameter of more than 30 nm when dried include: anatase, rutile and the like types of calcinated titanium oxide for pigment use obtained by means of thermal hydrolysis; calcinated powder of a titanium hydroxide or titania sol obtained by a neutralization method or an ion exchange method; and grown crystals of a titanium hydroxide obtained during a hydrolysis step or by autoclaving.

According to the present invention, a source of silicon dioxide is used as a lightening agent (or a bulk density reducing agent) and as a binder. A desirable material as the source of silicon dioxide eligible for use in the present invention may be in the form of a solution or silica sol which has a good dispersion ability. Examples of such desirable material include for instance silicic acid which is obtained by subjecting a sodium silicate or a potassium silicate to a neutralization or a cation exchange method, organic silicon compounds such as an ethyl silicate and acid hydrolyzates thereof, a quaternary ammonium silicate and an acid hydrolyzate thereof, colloidal silica and the like.

Of these, colloidal silica is most preferable because of its stability at a high concentration for a long period of time. When a colloidal silica preparation contains sodium as a stabilizer, it is preferable to remove sodium in advance by means of cation exchange, ultrafiltration or the like. A colloidal silica preparation having a particle size of 50 nm or larger may be useful as a bulk density reducing agent, but it has an inferior capacity a; a binder. Gel-form materials, such as a hydrogel obtained by neutralizing a sodium silicate and powdered gel preparations including a white carbon and an aerogel, are not preferable as the source of silicon dioxide because such materials not only have poor dispersion ability and inferior capacity as a binder but also reduce the catalytic effect of simultaneously added boron compound (or boron oxide).

A source of vanadium oxide eligible for use in the present invention may be selected from water soluble compounds which form vanadium oxide when calcinated in the air, such as ammonium metavanadate, vanadyl sulfate (or vanadium oxysulfate), vanadium formate, vanadium acetate, vanadyl oxalate, ammonium vanadium oxalate, vanadyl phosphate a vanadium oxyhalide and the like. Of these, vanadyl sulfate, ammonium metavanadate and vanadyl oxalate may preferably be used.

Examples of the source of alkali metal oxide eligible for use in the present invention include hydroxides, sulfates, carbonates, chlorides, nitrates, oxihalides, thiosulfates, nitrites, sulfites, hydrogensulfites, hydrogensulfates, oxalates, hydrogenoxalates and the like of potassium, cesium, rubidium and other alkali metals. Of these, hydroxides, sulfates and carbonates ma/ be used preferably.

Examples of sulfuric acid compounds as the source of sulfuric anhydride include sulfuric acid, ammonium sulfate, ammonium hydrogensulfate and the like. Of these, sulfuric acid and ammonium sulfate may be used preferably.

According to the present invention, such a vanadium compound, an alkali metal compound and a sulfuric acid compound are used as active components.

A boron compound eligible for use in the present invention as the source of boron oxide may be selected from soluble compounds such as boron oxide, boric acid, potassium tetraborate, potassium pentaborate, potassium metaborate, ammonium metaborate, ammonium tetraborate and the like, preferably from boric acid and ammonium metaborate because of their relatively high solubilities. A boron compound (or boron oxide) imparts not only an effect of improving strength of catalyst (abrasion resistance) markedly but also an effect of improving selectivity for the reaction products. In other words, a catalyst may have excellent activity, selectivity and abrasion resistance when it is produced by using active components and a titanium hydroxide which is capable of forming titanium oxide having a crystallite diameter of not more than 30 nm when dried at about 300° C. According to the present invention, strength of the catalyst and selectivity for the reaction products of the catalyst are further improved by the effect of the use of a boron compound in spite of the accelerated formation of titanium oxide crystals at the time of calcination of the catalyst composition.

The process for the production of the catalyst of the present invention comprises steps of mixing the foregoing component materials, spray drying the mixture and calcinating the spray-dried powder. Since mixing order of each component is optional, various mixing methods may be applicable such as simultaneous dissolving of two or more materials, dissolving of active components in a titanium hydroxide disperse liquid and the like.

Also, it is possible to use, as a source of titanium oxide, a mixture of a titanium hydroxide, which is capable of forming titanium oxide having a crystallite diameter of not more than 30 nm when dried, with another titanium compound such as a compound that forms titanium oxide having a crystallite diameter of larger than 30 nm.

If necessary, concentration of a slurry mixture thus prepared may be adjusted to an appropriate level by means of evaporation, prior to subjecting the mixture to the spray drying step to obtain spherical fine particles. The spray drying step may be effected by employing commonly used means. Preferably, spray drying may be carried out under such conditions that a weight average particle size of the resulting spherical fine particles is controlled within the range of from 40 to 150 μm. The spherical fine particles thus obtained are then calcinated in the air preferably at a temperature of from 300° to 700° C., more preferably from 400° to 600° C., and preferably for 1 to 6 hours, more preferably for 2 to 4 hours.

By carrying through these steps of the process of the present invention, a catalyst having the following properties may preferably be obtained.

Bulk density (g/cm$^3$): 0.5 to 1.3
Specific surface area (m$^2$/g): 5 to 60
Pore volume (cm$^3$/g): 0.1 to 0.6
Abrasion rate (wt %/15 Hr); 5 or less
Weight average particle size (μm): 40 to 150

In this instance, abrasion rate is measured by the ACC (American Cyanamid Co.) method described in B.P.737,429.

The catalyst obtained in the present invention can be applied preferably to a process for the production of a caboxylic anhydride from a corresponding aromatic hydrocarbon by means of a gas phase oxidation. Typical examples of such aromatic hydrocarbons include benzene, xylene, cumene, pseudocumene, durene and mixtures thereof. Consequently, the catalyst obtained by the process of the present invention can be used for the oxidation of: benzene into maleic anhydride, pseudocumene into trimellitic anhydride, durene into pyromellitic anhydride, and o-xylene or naphthalene into phthalic anhydride.

A hydrocarbon source for the production of phthalic anhydride by the use of the catalyst of the present invention may be o-xylene, naphthalene, and the like, preferably, o-xylene, more preferably an aromatic hydrocarbon which contains at least 10 mol % or more of o-xylene. For this reason, a process for the production of phthalic anhydride from o-xylene is described in the following as an illustrative example of the application of the catalyst of the present invention. This example, however, is in no way to be taken as limiting.

For the purpose of performing oxidation of o-xylene or naphthalene into phthalic anhydride, air may be used preferably as the source of oxygen taking various conditions into consideration, though not specifically restricted. A gas mixture which comprises oxygen and a dilution gas such as a nitrogen/carbon dioxide dilution gas, as well as an air system supplemented with oxygen, may also be useful as the source of oxygen.

The oxygen-containing gas source (air for example) may preferably be subjected to a preheating step (for example at 100° to 300° C.) prior to introduction into a reactor.

The oxidation reaction can be carried out at, over or below the atmospheric pressure Generally, the reaction may preferably be carried out at an atmospheric pressure of from 0.5 to 3.0. Preferably, the oxidation reaction may be carried out at a reaction temperature of from 300° to 450° C. The catalyst may preferably be used in an amount of from 10 to 30 kg/(kg-material gas/hour). Preferable ratio of a air to material, as in the reaction gas mixture may be in the range of from 5 to 15 kg/kg.

EXAMPLES

The present invention will now be described by way of the following examples which should be regarded as illustrative rather than restrictive.

Example 1

A 600 kg portion of a titanyl sulfate aqueous solution containing 5% by weight of titanium as TiO$_2$ was cooled to 12° C. and then neutralized by gradually adding 140 kg of 15% by weight aqueous ammonia spending about 10 minutes with thorough stirring to obtain a titanium hydroxide gel. The thus obtained gel showed a pH value of 8.5 and a temperature of 25° C.

A 20 kg portion of the gel slurry was subjected to dehydration under a reduced pressure using a plate filter, and 300 dm$^3$ of pure water was gradually added to the resulting gel cake in order to remove ammonium sulfate formed by the foregoing neutralization. Concentration of TiO$_2$ in the thus purified titanium hydroxide gel was found to be 11.8% by weight.

A portion of the purified gel was dried at a temperature of 300° C. and the resulting powder was subjected to X-ray diffraction. The crystallite diameter of anatase type titanium oxide in the powder was calculated to be 5.1 nm from a diffraction peak at an angle of $2\theta = 25.3°$ in the diffraction pattern.

To 100 kg of the aforementioned gel containing 11.8% by weight of TiO$_2$ obtained by the repeated washing using the plate filter was added 140 kg of pure water with thorough stirring to obtain a gel slurry containing 5.0% by weight of $TiO_2$.

A silica sol article having a mean particle size of 5 nm (Cataloid SI 550, manufactured by Catalysts & Chemicals Industries Co., Ltd.; consult Table 1 for its properties) was passed through a cation exchange resin layer to obtain 200 kg of Na-removed silica sol. The thus obtained Na-removed silica sol contained 10.3% by weight of $SiO_2$ with a $Na_2O/SiO_2$ weight ratio of 0.002.

A 600 dm$^3$ capacity stainless steel vessel equipped with a steam jacket was charged with the whole amount of the previously prepared gel slurry containing 5.0% by weight of $TiO_2$ and, with stirring, charged further with 97.5 kg of the just described Na-removed silica sol, 7.82 kg of a vanadyl sulfate aqueous solution containing 19.3% by weight of vanadium as $V_2O_5$ and 2.36 kg of a cesium sulfate aqueous solution containing 50.0% by weight of cesium as $Cs_2SO_4$ in that order. To the resulting mixture was added 0.97 kg of ammonium sulfate crystals and, finally, 80 kg of a previously prepared boric acid aqueous solution (2.8% by weight as $H_3BO_3$ concentration). This mixture showed a pH value of 2.5.

The thus obtained slurry mixture was heated with thorough stirring to evaporate water and concentrate the slurry to a level of 20% by weight as "$TiO_2+SiO_2+V_2O_5+Cs_2SO_4+SO_3+B_2O_3$". Thereafter, the concentrated slurry was dispersed thoroughly using a homogenizer and applied to a disk type spray dryer, and the resulting spray-dried powder was further dried overnight at 150° C. and then calcinated at 570° C. for 3 hours to obtain a catalyst which was named catalyst A. Chemical composition and physical properties of the catalyst are shown in Table 2.

Example 2

The process of Example 1 was repeated except that the amount of boron oxide was changed to obtain catalyst B, with its chemical composition and physical properties shown in Table 2.

Example 3

The process of Example 1 was repeated except that the amount of boron oxide was changed to obtain catalyst C, with its chemical composition and physical properties shown in Table 2.

Comparative Example 1

The process of Example 1 was repeated except that the source of $B_2O_3$ was not used to obtain catalyst D, with its chemical composition and physical properties shown in Table 2.

Comparative Example 2

The process of Example 1 was repeated except that the amount of boron oxide was changed to the highest level to obtain catalyst E, with its chemical composition and physical properties shown in Table 2.

Example 4

A metatitanic acid slurry, which is obtained as an intermediate product of a process for the production of titanium oxide for pigment use, was diluted and subjected to neutralization and washing steps in the same manner as in Example 1 to obtain a titanium hydroxide gel from which sulfuric acid was removed. Concentration of $TiO_2$ in the gel was found to be 29.0% by weight. When a portion of the thus prepared gel was dried at 300° C., the resulting powder showed a crystallite diameter of 16 nm. A powder preparation containing silicon dioxide, active components and boron oxide was prepared from the gel by similar means to the case of catalyst A, and the powder was calcinated at 600° C. for 3 hours to obtain catalyst F. Chemical composition and physical properties of this catalyst are shown in Table 2.

Example 5

The titanium hydroxide gel obtained in Example 4 was diluted with pure water to a gel concentration of 15% by weight, and the diluted gel was adjusted to pH 2 with nitric acid. The resulting slurry was heated at 180° C. for 100 hours with stirring using an external heating type autoclave. When a portion of the thus heated slurry was dried at 300° C., the resulting powder showed a crystallite diameter of 35 nm. In the same manner as in Example 1, catalyst G having properties as shown in Table 2 was obtained from the thus prepared titanium hydroxide slurry.

Example 6

A commercial article of anatase type titanium oxide powder (A#200, manufactured by Teikoku Kako Co., Ltd.) was suspended in pure water to prepare a slurry containing 30% by weight of titanium as $TiO_2$, and catalyst H having properties as shown in Table 2 was obtained from the thus prepared slurry in the same manner as in Example 1.

Example 7

A 200 dm$^3$ capacity stainless steel vessel equipped with a steam jacket was charged with compounds in the following order: 53.5 kg of the titanium hydroxide gel used in Example 1, the same amount of pure water, 9.5 kg of a silica sol article as shown in Table 1 having a mean particle size of 17 nm (Cataloid S-20L, manufactured by Catalysts & Chemicals Industries Co., Ltd.; $SiO_2$ contents, 20.5% by weight), 2.95 kg of a vanadyl sulfate aqueous solution containing 19.3% by weight of vanadium as $V_2O_5$, 0.45 kg of potassium sulfate crystals (purity, 99% by weight), 0.37 kg of ammonium sulfate crystals and 30 kg of a boric acid aqueous solution containing 1.6% by weight of boron as $B_2O_3$. The resulting slurry was concentrated to a level of 16% by weight as "$TiO_2+SiO_2+V_2O_5+K_2SO_4+SO_3+B_2O_3$", and the concentrated slurry was subjected to spray drying and drying/calcination steps in the same manner as in Example 1 to obtain catalyst I, with its chemical composition and physical properties shown in Table 2.

Example 8

A tank charged with 53.5 kg of the above titanium hydroxide gel was further charged with 5.6 kg of a silica sol article having a mean particle size of 26 nm (Cataloid SI-50; cf. Table 1 for its properties) which has been passed through a cation exchange resin layer to remove Na, 2 7 kg of a vanadyl sulfate aqueous solution, 1.0 kg of cesium sulfate, 0.35 kg of ammonium sulfate crystals and 30.5 kg of a boric acid aqueous solution (contents as $B_2O_3$, 1.6% by weight), and the resulting mixture was treated in the same manner as in Example 1 to obtain catalyst J, with its chemical composition and physical properties shown in Table 2.

Example 9

The same titanium hydroxide gel containing tank as described above was charged with 17.5 kg of a silica sol article as shown in Table 1 (Cataloid S-20L), 6.4 kg of a vanadyl sulfate aqueous solution, 0.9 kg of cesium sulfate, 0.38 kg of ammonium sulfate crystals and 30.5 kg of a boric acid aqueous solution, the resulting slurry was concentrated with stirring to a slurry concentration of 21% by weight, the thus concentrated slurry was subjected to spray drying and, thereafter, the resulting powder was treated in the same manner as in Example 1 to obtain catalyst K. Chemical composition and physical properties of this catalyst are shown in Table 2.

Comparative Example 3

Catalyst L was prepared by repeating the process for the production of catalyst A in Example 1 using the same titanium hydroxide gel except that the silica sol article was not used. Chemical composition and physical properties of this catalyst are shown in Table 2.

Example 10

A mixture of 500 kg of a titanyl sulfate aqueous solution containing 5% by weight of titanium as $TiO_2$ with 80.6 kg of an Na-removed silica sol having an $SiO_2$ concentration of 10.3% by weight obtained from a silica gel article (Cataloid SI-550; cf. Table 1) was cooled to 10° C. and then neutralized by gradually adding 128 kg of 15% by weight aqueous ammonia spending about 13 minutes with thorough stirring to obtain a coprecipitation gel of titanium hydroxide and silica. The thus obtained gel showed a pH value of 9.1 and a temperature of 22° C. The gel slurry thus obtained was subjected to dehydration and washing using a plate filter. Concentration of solid contents in the thus purified coprecipitation gel was found to be 9.5% by weight.

When a portion of the purified gel was dried at a temperature of 300° C., the crystallite diameter of anatase type titanium oxide in the resulting powder was found to be 4.0 nm. With stirring, pure water was added to 350 kg of the coprecipitation gel to obtain a gel slurry containing 5% by weight of solid contents.

The resulting slurry was mixed thoroughly with 120 kg of the aforementioned Na removed silica sol, 15.0 kg of a vanadyl sulfate aqueous solution, 5.0 kg of a $Cs_2SO_4$ aqueous solution, 2.0 kg of ammonium sulfate crystals and 175 kg of a 2.8% by weight boric acid aqueous solution. The thus obtained slurry mixture was heated to evaporate water and concentrate the slurry to a level of 17.8% by weight as "$TiO_2+SiO_2+V_2O_5+Cs_2SO_4+SO_3+B_2O_3$". Thereafter, the concentrated slurry was subjected to spray drying and calcination in the same manner as in Example 1 to obtain a catalyst which was named catalyst M. Chemical composition and physical properties of this catalyst are shown in Table 2.

Example 11

In the same manner as in the case of catalyst A, a mixture was prepared from the titanium hydroxide gel, silica sol, vanadyl sulfate aqueous solution, cesium sulfate aqueous solution, ammonium sulfate crystals and boric acid aqueous solution. The mixture was further mixed with a lanthanum nitrate aqueous solution and then subjected to spray drying and calcination to obtain catalyst N, with its chemical composition and physical properties shown in Table 2.

Example 12

Catalysts A to N obtained in Examples 1 to 11 and Comparative Examples 1 to 3 were subjected to a production test of phthalic anhydride from o-xylene by means of a gas phase oxidation using a fluidized bed reactor (made of SUS 304 stainless steel, 83 mm$\phi$ × 3400 mmL), with the results shown in Table 3. Unreacted o-xylene and reaction products including phthalic anhydride, phthalides, trialdehydes, maleic anhydride and $CO+CO_2$ were analyzed by gas chromatography.

| <Reaction conditions> | |
|---|---|
| Feed rate of o-xylene | 230 g/Hr (sulfur contents, 1000 ppm; nitrogen contents, 500 ppm) |
| Air volume | 2200 standard state dm$^3$/Hr |
| Linear velocity (empty reactor basis) | 17 cm/sec |
| Air/o-xylene ratio | 12.2 kg/kg |
| Pressure | 1.0 kg/cm$^2$ · G |
| Reaction temperature | 340° C. |
| Catalyst volume | 5000 cm$^3$ |

Conversion ratio of o-xylene, selectivity for phthalic anhydride and yield of phthalic anhydride were calculated based on the following formulae.

Conversion ratio of o-xylene (mol %) =

$$\frac{\text{gram mol of reacted o-xylene}}{\text{gram mol of supplied o-xylene}} \times 100$$

Selectivity for phthalic anhydride (mol %) =

$$\frac{\text{gram mol of formed phthalic anhydride}}{\text{gram mol of reacted o-xylene}} \times 100$$

Yield of phthalic anhydride (mol %) =

$$\frac{\text{gram mol of formed phthalic anhydride}}{\text{gram mol of supplied o-xylene}} \times 100$$

Example 13

A production test of phthalic anhydride from naphthalene by means of a gas phase contact oxidation was carried out using the same fluidized bed reactor used in Example 12, with the results shown in Table 3. Analysis and calculation of the results were carried out in the same manner as in the case of Example 12.

| <Reaction conditions> | |
|---|---|
| Feed rate of naphthalene | 275 g/Hr (sulfur contents, 1000 ppm; nitrogen contents, 500 ppm) |
| Air volume | 2200 standard state dm$^3$/Hr |
| Linear velocity (empty reactor basis) | 16 cm/sec |
| Air/naphthalene ratio | 10.3 kg/kg |
| Pressure | 1.0 kg/cm$^2$ · G |
| Reaction temperature | 330° C. |
| Catalyst volume | 5000 cm$^3$ |

TABLE 1

| | Properties of silica sol materials | | | | |
|---|---|---|---|---|---|
| Name | SiO$_2$ conc. % | Na$_2$O conc. % | Specific surface area m$^2$/g | Particle size nm | Catalyst applied |
| Cataloid | 20.2 | 0.75 | 530 | 5.1 | A, B, C, |
| SI-550 | | (0.002) | | | D, E, F, G, H, M, N |
| Cataloid S-20L | 20.5 | 0.04 | 146 | 18.7 | I, K |
| Cataloid SI-50 | 47.8 | 0.61 (0.002) | 103 | 26.5 | J |

(Note) SI-550 and SI-50 were subjected to Na-removal using an ion exchange resin prior to their use, while S-20L was used per se. Parenthesis indicates Na$_2$O/SiO$_2$ weight ratio after Na-removal.

TABLE 2

Chemical compositions and physical properties of catalysts

| Example No. | Catalyst No. | V$_2$O$_5$ wt % | M$_2$SO$_4$ wt % | SO$_3$ wt % | La$_2$O$_3$ wt % | TiO$_2$ wt % | B$_2$O$_3$ wt % | SiO$_2$ wt % | SO$_3$/M$_2$O molar ratio | M$_2$O/V$_2$O$_5$ molar ratio | SiO$_2$/TiO$_2$ weight ratio | B$_2$O$_3$/TiO$_2$ weight ratio | V$_2$O$_5$ + M$_2$O + SO$_3$ wt % |
|---|---|---|---|---|---|---|---|---|---|---|---|---|---|
| 1 | A | 5.7 | 4.5 | 2.2 | — | 44.8 | 4.8 | 38.1 | 3.2 | 0.40 | 0.85 | 0.11 | 11.4 |
| 2 | B | 5.9 | 4.6 | 2.3 | — | 46.2 | 1.8 | 39.3 | 3.3 | 0.39 | 0.85 | 0.04 | 11.8 |
| 3 | C | 5.0 | 4.0 | 1.9 | — | 39.5 | 16.0 | 33.6 | 3.1 | 0.40 | 0.85 | 0.41 | 10.0 |
| Comparative 1 | D | 6.0 | 4.7 | 2.3 | — | 47.0 | — | 40.0 | 3.2 | 0.39 | 0.85 | 0 | 12.0 |
| Comparative 2 | E | 4.6 | 3.6 | 1.8 | — | 36.2 | 23.0 | 30.8 | 3.3 | 0.39 | 0.85 | 0.64 | 9.2 |
| 4 | F | 5.7 | 4.4 | 2.2 | — | 45.0 | 4.9 | 37.8 | 3.3 | 0.39 | 0.84 | 0.11 | 11.3 |
| 5 | G | 5.8 | 4.5 | 2.2 | — | 43.0 | 8.2 | 36.3 | 3.2 | 0.39 | 0.85 | 0.19 | 11.5 |
| 6 | H | 5.7 | 4.5 | 2.1 | — | 38.5 | 17.1 | 32.1 | 3.1 | 0.40 | 0.83 | 0.44 | 11.3 |
| 7 | I | 5.7 | K$_2$SO$_4$ 4.5 | 2.2 | — | 63.3 | 4.8 | 19.5 | 2.1 | 0.82 | 0.31 | 0.08 | 10.3 |
| 8 | J | 5.2 | 4.9 | 2.1 | — | 55.9 | 4.9 | 27.0 | 2.9 | 0.61 | 0.48 | 0.09 | 11.1 |
| 9 | K | 12.3 | 4.4 | 2.3 | — | 40.3 | 4.9 | 35.8 | 3.4 | 0.96 | 0.89 | 0.12 | 18.0 |
| Comparative 3 | L | 6.0 | 4.6 | 2.4 | — | 82.0 | 5.0 | — | 3.4 | 0.39 | 0 | 0.06 | 12.0 |
| 10 | M | 5.3 | 4.5 | 2.2 | — | 45.1 | 5.0 | 37.9 | 3.2 | 0.43 | 0.84 | 0.11 | 11.0 |
| 11 | N | 5.6 | 4.4 | 2.1 | 2.6 | 43.6 | 4.6 | 37.1 | 3.2 | 0.51 | 0.85 | 0.11 | 11.1 |

| Example No. | Catalyst No. | Specific surface area m$^2$/g | Pore volume cm$^3$/g | Bulk density g/cm$^3$ | Abrasion rate wt % | Crystallite diameter nm | Crystallite diameter after drying* nm |
|---|---|---|---|---|---|---|---|
| 1 | A | 23 | 0.39 | 0.86 | 0.8 | 40 | 5.1 |
| 2 | B | 46 | 0.55 | 0.70 | 2.2 | 34 | 5.1 |
| 3 | C | 7 | 0.17 | 1.25 | 0.2 | 58 | 5.1 |
| Comparative 1 | D | 120 | 0.71 | 0.60 | 7.9 | 23 | 5.1 |
| Comparative 2 | E | 3 | 0.08 | 1.53 | 0.1 | 71 | 5.1 |
| 4 | F | 11 | 0.42 | 0.82 | 2.7 | 55 | 16.0 |
| 5 | G | 10 | 0.29 | 0.67 | 4.9 | 52 | 35.0 |
| 6 | H | 2 | 0.27 | 0.55 | 5.0 | 93 | 89.0 |
| 7 | I | 13 | 0.20 | 1.12 | 0.7 | 50 | 5.1 |
| 8 | J | 19 | 0.34 | 0.99 | 0.6 | 44 | 5.1 |
| 9 | K | 14 | 0.23 | 1.10 | 0.5 | 48 | 5.1 |
| Comparative 3 | L | 2 | 0.05 | 1.68 | 0.1 | 81 | 5.1 |
| 10 | M | 40 | 0.48 | 0.74 | 0.6 | 35 | 4.0 |
| 11 | N | 30 | 0.40 | 0.83 | 0.9 | 37 | 5.1 |

*Crystallite diameter of titanium hydroxide after drying at 300° C.

TABLE 3

Results of the gas phase oxidation reaction of o-xylene and naphthalene

| Example No. (Catalyst) | Naphthalene as starting material | | | | o-Xylene as starting material | | | |
|---|---|---|---|---|---|---|---|---|
| | Conversion rate of naphthalene (mol %) | Selectivity for phthalic anhydride (mol %) | Yield of phthalic anhydride (mol %) | Yield of phthalic anhydride (wt %) | Conversion rate of o-xylene (mol %) | Selectivity for phthalic anhydride (mol %) | Yield of phthalic anhydride (mol %) | Yield of phthalic anhydride (wt %) |
| 1 (A) | 65.4 | 87.2 | 83.2 | 72.0 | 92.7 | 74.9 | 69.4 | 96.9 |
| 2. (B) | 96.1 | 82.7 | 79.5 | 68.8 | 94.3 | 64.2 | 60.5 | 84.5 |
| 3 (C) | 80.3 | 84.3 | 67.7 | 58.6 | 70.2 | 79.9 | 56.1 | 78.3 |
| CE1 (D) | 98.0 | 47.0 | 46.1 | 39.9 | 98.2 | 39.4 | 38.7 | 54.0 |
| CE2 (E) | 65.2 | 80.4 | 52.4 | 45.3 | 62.6 | 67.1 | 42.0 | 58.6 |
| 4 (F) | 85.2 | 86.1 | 73.4 | 63.5 | 79.7 | 56.0 | 44.6 | 62.3 |

TABLE 3-continued

| | Results of the gas phase oxidation reaction of o-xylene and naphthalene | | | | | | | |
|---|---|---|---|---|---|---|---|---|
| | Naphthalene as starting material | | | | o-Xylene as starting material | | | |
| Example No. (Catalyst) | Conversion rate of naphthalene (mol %) | Selectivity for phthalic anhydride (mol %) | Yield of phthalic anhydride (mol %) | Yield of phthalic anhydride (wt %) | Conversion rate of o-xylene (mol %) | Selectivity for phthalic anhydride (mol %) | Yield of phthalic anhydride (mol %) | Yield of phthalic anhydride (wt %) |
| 5 (G) | 90.2 | 75.4 | 68.0 | 58.8 | 86.9 | 65.2 | 56.7 | 79.2 |
| 6 (H) | 60.5 | 75.2 | 45.5 | 39.4 | 53.7 | 70.6 | 37.9 | 52.9 |
| 7 (I) | 90.3 | 80.7 | 72.9 | 63.1 | 88.6 | 70.8 | 62.7 | 87.5 |
| 8 (J) | 95.7 | 86.1 | 82.4 | 71.3 | 94.0 | 67.4 | 63.4 | 88.5 |
| 9 (K) | 100 | 65.3 | 65.3 | 56.5 | 97.2 | 51.0 | 49.6 | 69.2 |
| CE3 (L) | 78.4 | 82.6 | 64.8 | 56.1 | 72.5 | 59.6 | 43.2 | 60.3 |
| 10 (M) | 95.4 | 87.3 | 83.3 | 72.1 | 91.6 | 74.0 | 67.8 | 94.6 |
| 11 (N) | 98.3 | 90.4 | 88.9 | 76.9 | 94.7 | 78.7 | 74.5 | 109.8 |

It is evident from the above results that catalyst L (Comparative Example 3) which does not contain $SiO_2$ in its carrier cannot be used suitably as a fluid catalyst because of its markedly high bulk density. It is evident also that catalyst D (Comparative Example 1) which contains no $B_2O_3$ in its carrier has extremely large specific surface area and markedly high abrasion rate (low abrasion resistance or weak strength), thus showing considerably low product selectivity. Too much content of $B_2O_3$ (catalyst ( or Comparative Example 2), however, showed a high bulk density and a low pore volume and resulted in a low product yield.

Thus, it is apparent that there has been provided, in accordance with the present invention, a catalyst which is possessed of not only high activity, high product selectivity and high abrasion resistance (strength) but also suitable bulk density for fluidization, while these excellent properties cannot be found in commonly used catalysts for use in the production of carboxylic anhydrides from hydrocarbons such as o-xylene and naphthalene by means of fluidized bed gas phase oxidation.

Although some preferred embodiments have been described, many modifications and variations may be made thereto in the light of the above teachings. It is therefore to be understood that within the scope of the appended claims, the invention may be practiced otherwise than as specifically described.

We claim:

1. A fluid catalyst for use in gas phase oxidation of an aromatic hydrocarbon consisting essentially of;
   50 to 95% by weight, calculated as $TiO_2 + SiO_2 + B_2O_3$, of component (A) which comprises titanium oxide, silicon dioxide and boron oxide and
   5 to 50% by weight calculated as $V_2O_5 + M_2O$, wherein M is an alkali metal $+ SO_3$ of component (B) comprising vanadium oxide, an alkali metal oxide and sulfuric anhydride, wherein the weight ratios of $B_2O_3$ to $TiO_2$ and $SiO_2$ to $TiO_2$ in component (A) are in the range of 0.02 to 0.5 and 0.25 to 1.0, respectively, and wherein the weight ratios of $SO_3$ to $M_2O$ and $M_2O$ to $V_2O_5$ in component (B) are in the range of 0.1 to 6.0 and 0.1 to 5.0, respectively,
   wherein said $V_2O_5$ in the catalyst is in the range of 1 to 30% by weight,
   and wherein said catalyst is prepared using a titanium oxide source capable of forming titanium oxide having a crystallite diameter of not more than 30 nm when dried at a temperature of about 300° C.,
   and wherein said catalyst is prepared by a process which comprises the steps of
   (a) mixing compounds as respective sources of titanium oxide, silicon dioxide, boron oxide, vanadium oxide, alkali metal oxide, and sulfuric anhydride,
   (b) spray drying the mixture of step (a) and
   (c) calcinating the spray dried powder of step (b).

2. The fluid catalyst of claim 1 wherein said alkali metal oxide is at least one oxide of an alkali metal selected from the group consisting of potassium, cesium and rubidium.

3. The fluid catalyst of claim 1 wherein said catalyst has a bulk density of 0.5 to 1.3 g/cm$^3$, a specific surface area of 5 to 60 m$^2$/g, a pore volume of 0.1 to 0.6 cm$^3$/g, an abrasion rate of not more than 5% by weight per 15 hours and a weight average particle size of 40 to 150 um.

4. The fluid catalyst of claim 1 wherein said source of silicon dioxide is colloidal silica.

5. The fluid catalyst of claim 1 wherein said source of vanadium oxide is a compound selected from the group consisting of vanadyl sulfate, ammonium metavanadate and vanadyl oxalate.

6. The fluid catalyst of claim 1 wherein said source of alkali metal oxide is a compound selected from the group consisting of hydroxides, sulfates and carbonates of potassium, cesium and rubidium.

7. The fluid catalyst of claim 1 wherein said source of sulfuric anhydride is sulfuric acid or ammonium sulfate.

8. The fluid catalyst of claim 1 wherein said source of boron oxide is boric acid or ammonium metaborate.

* * * * *

UNITED STATES PATENT AND TRADEMARK OFFICE
CERTIFICATE OF CORRECTION

PATENT NO. : 5,185,309
DATED : February 9, 1993
INVENTOR(S) : AONO et al

It is certified that error appears in the above-identified patent and that said Letters Patent is hereby corrected as shown below:

Column 15, line 56, change "weight ratios" to

--molar ratios--

Signed and Sealed this

Twelfth Day of September, 1995

Attest:

BRUCE LEHMAN

Attesting Officer

Commissioner of Patents and Trademarks